United States Patent [19]

Jones

[11] 4,092,340

[45] May 30, 1978

[54] PROCESS FOR PREPARING ORGANOTIN COMPOUNDS

[75] Inventor: Trevor Eric Jones, Halesowen, England

[73] Assignee: Albright & Wilson Limited, Warley, England

[21] Appl. No.: 648,948

[22] Filed: Jan. 14, 1976

[30] Foreign Application Priority Data

Jan. 20, 1975 United Kingdom ............... 02456/75

[51] Int. Cl.$^2$ ............................................... C07F 7/22
[52] U.S. Cl. ................................................. 260/429.7
[58] Field of Search .................................... 260/429.7

[56] References Cited

U.S. PATENT DOCUMENTS

| | | | |
|---|---|---|---|
| 2,679,506 | 5/1954 | Rochow | 260/429.7 |
| 2,852,543 | 7/1958 | Blitzer et al. | 260/429.7 |
| 3,085,102 | 4/1963 | Yatagai et al. | 260/429.7 |
| 3,415,857 | 12/1968 | Hoye | 260/429.7 |
| 3,475,473 | 10/1960 | Tahara et al. | 260/429.7 |
| 3,547,965 | 12/1970 | Takubo et al. | 260/429.7 |
| 3,651,108 | 3/1972 | Giannaccari et al. | 260/429.7 |
| 3,954,820 | 5/1976 | Menon | 260/429.7 |

FOREIGN PATENT DOCUMENTS

736,822  9/1955  United Kingdom.

OTHER PUBLICATIONS

Chemical Abstracts, v33, 5357$^3$ (1939).
Chemical Abstracts, v35, 2470 (1941).
JACS, v75, pp. 4103–4105 (1953).
Chemical Abstracts, v38, 61$^4$ (1944).
Van Der Kerk et al., J. Appl. Chem. v4, pp. 307–313 (1954).
Luijten et al, Investigations in the Field of Organotin Chemistry Tin Res. Inst. England, pp. 11 to 13, 25 to 33, 85 & 86 (1955).
Lietz et al., J. Org. Chem. v22, pp. 60–62 (1957).
Sawyer, Organotin Compounds, Marcel–Dekker, Inc., N.Y., v1, pp. 82–84 (1971).

*Primary Examiner*—Helen M. S. Sneed
*Attorney, Agent, or Firm*—Flynn & Frishauf

[57] ABSTRACT

Tetraalkyltin compounds substantially free from tin, tin alkyl and di alkyl contaminants are prepared by reacting an alkyl halide of 1 – 4 carbon atoms with tin in the presence of an 'onium salt e.g. a quaternary ammonium halide and at least 0.5 g atom of zinc per g atom of tin, and collecting a vapor phase effluent comprising the tetraalkyltin. The tetraalkyltin can be disproportionated with stannic chloride to give alkyltin chlorides, intermediates for making stabilizers for polymers and biocides.

28 Claims, No Drawings

PROCESS FOR PREPARING ORGANOTIN COMPOUNDS

This invention relates to a process for preparing tetraorganotin compounds from elemental tin.

Organotin compounds can be prepared by reaction of tin halides with organo-metallic compounds such as Grignard reagents. Processes have also been described in which organotin compounds are prepared directly from elemental tin. Thus our British patent specification No. 1115646 describes a process for preparing predominantly diorganotin dihalides which comprises reacting tin with an aliphatic halide in the presence of a nitrogen, sulphur or phosphorus 'onium compound and a preformed tin halide or organotin halide and in the optional presence as co-catalyst of a small amount of a metal which may be zinc among many others. In U.S. Pat. No. 3,085,102 is described a similar process but without the 'onium compound and preformed halide, but in which the co-catalyst is essential and is preferably magnesium. U.S. Pat. No. 3,547,965 describes the preparation of triorganotin halides by reaction of organic halides with an equiatomic mixture of tin and zinc in the presence of an alcohol. U.S. Pat. No. 3,651,108 describes the preparation of tetra organotin compounds by reaction of organic halides in the presence of an 'onium compound, or Lewis base with tin and an alkaline or alkaline earth metal in particular magnesium.

We have now found a process for preparing tetraalkyltin compounds without using the hazardous alkaline or alkaline earth metals.

The present invention provides a process for preparing a tetraalkyltin compound, which comprises passing a halide of formula RX, wherein R is an alkyl group of 1 - 4 carbon atoms and X is a chlorine, bromine or iodine atom, into a heated suspension of metallic material which is zinc and tin, or an alloy of tin and zinc, the atomic proportion of zinc to tin in the material being at least 0.5 : 1, in a liquid comprising at least one organic quaternary ammonium or phosphonium salt or tertiary sulphonium salt, to produce a vapour effluent comprising substantially all the tetraalkyltin compound of formula $R_4Sn$, prepared.

The alkyl group in the alkyl halides is methyl, ethyl, n or isopropyl n-, sec- iso- or tert. butyl. The halogen X is preferably chlorine, as such halides give maximum difference in boiling points between the halide and the tetraalkyl tin product which aids separation of the tetraalkyltin from excess of alkyl halide in the effluent. This maximum difference in boiling points also occurs when the alkyl halide is a methyl halide. Methyl chloride is most preferred. A mixture of alkyl halides may be used to give a mixture of tetraalkyltin products. The amount of alkyl halide passed is usually at least 2 moles per g atom of tin and preferably 2.5 - 8 e.g. 2.5 - 5 moles per g atom of tin; the total amount of alkyl halide passed depends on the degree to which the reaction is taken to completion i.e. for 100% reaction at least 4 moles alkyl halide per g atom of tin or 2 moles per g atom of zinc (whichever is the smaller) is needed.

The liquid contains the organic quaternary ammonium, or phosphonium salt or tertiary sulphonium salt often at a temperature of 100° - 300° C preferably 110° - 220° C, and especially for reactions involving methyl halides 130° - 180° C e.g. 130° - 160° C and, especially for the other halides, 160° - 220° C. The temperature is such as to cause no decomposition of the salt and preferably no melting or sintering of the tin. The salt is usually a halide e.g. a chloride or bromide but especially an iodide; indeed, if the halide reactant is not itself an iodide, the presence of an iodide in the liquid is very desirable as it enhances the reaction rate. The salt is commonly a salt of formula $R'_4N^+ Y^-$, $R'_4P^+ Y^-$ or $R'_3S^+ Y^-$, wherein each R' is an alkyl group, e.g. of 1 - 13, especially 1 - 6, carbon atoms, or an aralkyl group of 7 - 19 carbon atoms, e.g. an aralkyl hydrocarbyl group of 7 - 19 carbon atoms, such as benzyl, or a cycloalkyl group of 5 - 7 carbon atoms, e.g. cyclohexyl or an aryl group, e.g. an aromatic hydrocarbyl group of 6 - 18 carbon atoms, such as phenyl, tolyl or naphthyl, and Y is a chloride, bromide or preferably an iodide ion. Examples of the salts are tetrabutyl ammonium and phosphonium halides, benzyltrimethyl ammonium and phosphonium halides and tetra octylammonium halides. The salt as such may be mixed with the tin and zinc or may be obtained by reaction in situ of the halide reactant of formula RX with the corresponding tertiary amine or phosphine or sulphide of formula $R'_3N$, $R'_3P$ or $R'_2S$ preferably before addition of the tin and zinc. The salt is preferably present in an amount of 0.1 to 0.6 and especially 0.15 to 0.3 molar proportions per atomic proportion of tin.

In addition to the salt the liquid contains tin and zinc which are preferably both solid, though if the temperature is high enough they are in the form of a molten alloy. The solid tin may be subdivided e.g. in the form of powder or communited material, or in sponge form but is usually in the form of discs. The solid zinc may also be subdivided e.g. in the form of powder or comminuted material but may be in the form of granules. The atomic ratio of zinc to tin is usually 0.5 : 1 to 3 : 1, preferably 1 : 1 to 3 : 1 e.g. 1.5 : 1 to 3.0 : 1, and especially 1.5 : 1 to 2.5 : 1; stoichiometry of the reaction suggests a ratio of about 2 : 1. While the tin and zinc are usually separate in elemental form, they may be in the form of a solid or liquid alloy consisting essentially of tin and zinc, usually in the desired atomic ratio for use in the process. The suspension is usually agitated e.g. by stirring.

If the melting point of the salt is below the reaction temperature, the molten salt can provide the necessary liquid phase for the reaction and is the sole organic liquid present, as is preferred. If desired an organic diluent may be present and should have a boiling point under the reaction pressure substantially higher than the reaction temperature, e.g. at least 50° C higher and be inert to the reactants. Examples of such diluents are high boiling paraffin oils of b.p. greater than 300° C, dodecane, tetradecane or tetralin. The diluent is needed to provide a liquid phase if the salt has a melting point higher than that of the reaction temperature or if the proportion of salt to the combined weight of tin and zinc is insufficient to provide an agitatable suspension. The minimum proportion of salt depends on the form of the tin and zinc; less salt can be used satisfactorily with powdered tin or zinc than with tin discs or zinc granules. However, where possible the reaction is carried out in the absence of any inert organic liquid diluent. The weight proportion of liquid phase to the combined total weight of zinc and tin is preferably 0.10 : 1 to 1 : 1, though higher proportions may be used; the proportion is more preferably 0.1 : 1 to 0.7 : 1.

The alkyl halide is passed into the hot liquid. The temperature and pressure conditions of the reaction are such that tetraalkyltin compound evaporates and forms part of the gaseous effluent from the reaction liquid. As the boiling point of the alkyl halides are very much less than those of the corresponding tetraalkyltin, any unreacted alkyl halide vapourizes forming part of the gaseous effluent. Accordingly the alkyl halide is usually added at least initially at a rate which is not very much faster than the rate of reaction in order to optimize the production of organotin without leaving too much unreacted alkyl halide in the gaseous effluent. It is desirable and preferably essential that the tetraalkyltin product is removed from the liquid by evaporation as soon as it is formed. Thus the reaction is carried out with continuous or continual passage of the alkyl halide and continuous collection of the gaseous effluent. When the temperature of the liquid is not above the boiling point of the tetraalkyltin product under atmospheric pressure, the reaction is carried out under a reduced pressure so that the tetraalkyltin evaporates. Preferably the pressure (reduced or otherwise) is such that the temperature of the liquid is at or above the boiling point of the tetraalkyltin under the pressure pertaining over the liquid. Pressures of 1 – 250 mm Hg can be used. Even if the temperature of the liquid is above the boiling point of the tetraalkyltin compound, a reduced pressure can be applied to the liquid if desired. For the production of tetramethyltin, a liquid temperature of 110° – 220° C and especially 130° – 180° C is suitable, for tetra ethyltin, a liquid temperature of 150° – 220° C, preferably 160° – 200° C under a pressure of 10 – 100 mm Hg, for tetrapropyltins, a liquid temperature of 150° – 220° C under 1 – 50 mm Hg pressure, and for tetra-n-butyltin a temperature of 150° – 220° C under 1 – 10 mm Hg pressure. The reaction temperature and reaction time are interrelated.

The reaction can be carried out to substantial completion which occurs when the tin or zinc is first completely reacted; which is first to be reacted depends on whether there is an atomic excess of zinc or tin over the stoichiometric atomic 2 : 1 ratio. The rate of reaction decreases substantially towards the end of the reaction so that it is preferred for a batch process being operated repeatedly or for a continuous process for the reaction to be taken to a maximum of 75% completion e.g. 40 – 70% and preferably 50 – 70% completion. Alternatively the rate of reaction can be maintained by stepwise addition of tin and zinc in the desired atomic ratio during the process.

The reaction time depends on the nature of the alkyl group and the halogen in the alkyl halide, the reaction temperature, the presence or absence of iodide ion in the reaction mixture, the proportion of 'onium catalyst and the degree to which the reaction is taken to completion. The reaction time is reduced with a decreasing carbon content in the alkyl group, an increasing atomic weight of the halogen, an increasing reaction temperature, the presence of iodide ion, an increasing amount of 'onium catalyst and a decreasing degree of reaction. However, reaction times of 2 to 24 hours at 140° – 180° C are often suitable for 40 – 70% reaction, e.g. 6 – 12 hr for methyl chloride. The alkyl halide is passed into the liquid suspension continuously or continually until the tin or zinc is first all reacted or until no further tetraalkyltin is prepared e.g. no fresh condensate of tetraalkyltin is made, or until the rate of production is very small.

The gaseous effluent comprises the tetraalkyltin product and unreacted alkyl halide. The tetraalkyltin product can be separated from the effluent e.g. by condensation leaving in the effluent unreacted halide, which in a continuous or repeated batch process can be recycled for reuse. The process of the invention is especially suitable for preparing tetramethyltin because in this case the product can be most easily separated from the reactant halide. In addition in the case of the methyl and ethyl halides, the corresponding tetra organotin compounds have a very high volatility at a reaction temperature of 130° – 180° C (in the case of tetraethyltin, with the aid of reduced pressure), so that the process of the invention can be used to prepare such compounds easily without the need for any high pressure equipment that would be needed if prior art processes involving reaction of the components in the liquid phase in an enclosed system were carried out at the present high temperatures. Low temperature condensers are needed for efficient recovery of tetramethyltin.

When the reaction has been taken to the desired degree of completion, the liquid contains the salt, any unreacted tin and any unreacted zinc, and byproduct zinc chloride. The liquid may be reused, preferably once the zinc chloride byproduct has been separated. Thus the reaction mixture once cold can be extracted with an organic solvent and any insoluble metal residue consisting of tin and/or zinc separated leaving a solution of quaternary or tertiary salt and zinc chloride; the metal residue can be mixed with the necessary amount of fresh tin and/or zinc for reuse. Examples of suitable solvents are dialkyl ketones of 3 – 6 carbon atoms, e.g. acetone, methyl ethyl ketone and methyl isobutyl ketone and alkanols of 1 – 6 carbon atoms, e.g. methanol, ethanol, propanols and butanols. The solution of salt and zinc chloride may be recycled for reuse as such; preferably the zinc chloride is separated by making use of solubility differences between it and the salt e.g. by addition of benzene in which the salt is soluble but zinc chloride insoluble. Thus the solvent in which the zinc chloride is insoluble can be added to the solution of salt and zinc chloride to precipitate the zinc chloride and leave a solution of the salt for evaporation of solvent and reuse of the salt.

The tetraalkyltin compounds are directly prepared by the process of this invention substantially free from catalyst residues and unreacted tin, in contrast to the process of U.S. Pat. No. 3,651,108, and substantially free from organic solvent in contrast to the product of the conventional Grignard process which usually is a solution of the tetra organotin in an ether solvent; the boiling points of tetramethyltin and tetrahydrofuran, a preferred ether solvent in the Grignard process, are sufficiently close that it is not economic to isolate the tetramethyltin from such a solution. The tetraalkyltin compounds made by the process of the invention usually contain less than 1% by weight in total of trialkyltin halide and dialkyltin dihalide and preferably less than 0.1%.

The tetraorganotin compounds may be used for preparing tri organotin halo compounds e.g. trialkyltin chlorides substantially free from di and mono organotin compounds by mixing the tetraorganotin compound with the appropriate molar proportion of stannic halide e.g. stannic chloride; similarly the corresponding dialkyl and monoalkyltin halides may be prepared. The organotin halides are used as antifungal compounds or as intermediates for making such compounds or stabilizers e.g. dimethyltin bis(isooctylthioglycollate), for polymeric materials e.g. PVC. In particular the tetraalkyltin compounds may be disproportionated with stannic chloride to give a 1 : 1 mixture of mono and trialkyltin halides, the latter can be disproportionated to a 1 : 1 mixture of mono and dialkyltin halides giving in total a 2 : 1 molar mixture of mono alkyltin trihalide and dialkyltin dihalide useful as an intermediate for making mixtures of stabilizers e.g. mercapto ester stabilizers for PVC.

The invention is illustrated in the following Examples 1 - 7.

EXAMPLE 1

Into a 250 ml. reaction vessel fitted with a stirrer, thermometer, sintered glass bubbler and still head leading to a condenser with a receiver and thence to two cold traps at $-40°$ C to $-50°$ C, was placed tin powder (118.7g., 1.0g. atom), zinc powder (130.7g. 2.0g atom), and tetrabutyl phosphonium iodide 77.2g (0.2 mole). The mixture of three components was stirred and heated to 150° - 160° C at which temperature the iodide salt was liquid. Methyl chloride gas was bubbled into the mixture at about 100 mls/min. After about 30 minutes a liquid (tetramethyltin) started to condense in the receiver. The heating, stirring and passage of the gas were continued for about 10 hours by which time about 126g (2.5 mole) of methyl chloride had been passed and no more fresh condensate was produced. The cold traps were allowed to warm up and their contents combined with that in the receiver. A combined total of 78.2g. (0.44 mole) of tetramethyltin was obtained; analysis by gas liquid chromatography of the tetramethyltin did not show the presence of any tri methyltin chloride or dimethyltin dichloride. The contents of the reaction vessel were extracted with acetone and a residue containing 0.49g atom unreacted tin and 0.83g atom unreacted zinc was separated. The acetone extract contained no tin, only iodide salt and zinc chloride. The yield of tetramethyltin was 86% (based on reacted tin) and 44% (based on tin supplied to the reaction).

EXAMPLE 2

The process was carried out as described in Example 1, but without the cold traps and with 118.7 g (1.0g mole) of tin powder, 78.0g (1.2 mole) of zinc powder and tetrabutylphosphonium iodide (71.2g., 0.184g mole) to replace the amounts in Example 1. The methyl chloride gas was passed at 150 ml/min. for about 8 hours until no more product condensed in the receivers. The combined total weight of tetramethyltin was 33 g, a yield of 18.5% based on the total of tin supplied to the reaction, but much tetramethyltin was lost by entrainment in the methyl chloride vapour and not condensed in the receiver. Gas liquid chromatographic analysis of the tetramethyltin product did not show the presence of any trimethyltin chloride or dimethyltin dichloride.

EXAMPLE 3

The process was carried out as described in Example 1 with the cold traps, but with 59.35g (0.5g atom) of tin powder, 65.35g (1.0g atom) of zinc powder, 77.2g (0.2 mole) tetrabutylphosphonium iodide and passage of a total of about 75g (1.5 mole) of methyl chloride over 6 hr replacing the amounts and reaction time in Example 1. The combined total weight of tetramethyltin condensate obtained was 55.0g (0.308 mole). The reaction liquid was worked up as in Example 1 and 0.16g atom of tin and 0.29 g atom of zinc were recovered. The yield of tetramethyltin was 62.0% based on tin supplied to the reaction and 91% based on tin reacted.

EXAMPLE 4

The process was carried out as described in Example 1 with the cold traps, but with 78.34g (0.66 atom) of tin powder, 86.91g (1.33g atom) of zinc powder. 47.6g (0.13 mole) of tetrabutyl phosphonium iodide and passage of a total of about 202g (4.0 mole) of methyl chloride over 13 hr, replacing the amounts and reaction time given in Example 1. The combined total weight of tetramethyltin condensate was 70.4g (0.39 mole), representing a yield of 59.3% based on tin supplied to the reaction.

EXAMPLE 5

Into a flask fitted with a stirrer, thermometer, dropping funnel and still head leading to a condenser with a receiver, was placed tin powder (59.35g, 0.5g atom), zinc powder (65.35g, 1g atom) and tetra n-butyl phosphonium iodide (38.6g, 0.1 mole) which was heated to 170° - 190° C and stirred. Ethylbromide (130.5g, 1.2 mole) was added dropwise over 6 hr, while the pressure was reduced to about 25 mm Hg. At the end of 6 hr, the receiver contained 26.7g (0.11 mole) of tetra ethyltin corresponding to a yield of 22.6% based on tin added to the reaction. The reaction was not taken to completion.

EXAMPLE 6

The reaction was carried out as described in Example 2 but with 59.35g tin powder (0.5g atom), 65.35g atom zinc powder (1.0g atom), 36.9g (0.1 mole) of tetrabutyl ammonium iodide and methyl chloride gas passed at 100 mls/min. for 5 hr. The reaction was carried out at 160° - 170° C. After 5 hr, which did not correspond to the end of the reaction, 5.8g of tetramethyltin (0.035 mole) was in the receiver, a yield of about 7% based on tin supplied to the reaction; as no cold traps were used, much tetramethyltin escaped uncollected.

EXAMPLE 7

The reaction was carried out as described in Example 6 but with tetrabutyl phosphonium iodide (38.6g, 0.1 mole) instead of the tetrabutyl ammonium iodide and a reaction temperature of 250° - 270° C, at which the tin was molten, and the zinc dissolved in the molten tin giving a molten alloy of tin and zinc. After 2 hr, when the reaction was far from complete, the reaction was stopped and 8.1g (0.045 mole) of tetramethyltin was obtained, a yield of 9% based on tin supplied to the reaction.

COMPARATIVE EXAMPLES

EXAMPLES A - D

A. An apparatus as described in Example 1 was set up and into the flask was placed 118.7g (1.0g atom) of tin powder, 73.8g (0.2 mole) of tetrabutylammonium iodide and 48.6g (2.0g atom) of magnesium to replace the zinc in Example 1. The flask was being heated up to 150° C prior to passage of methyl chloride gas when the contents of the flask decomposed violently.

B. When, on a quarter of the scale, the experiment was repeated with 148.5g (1.0g mole) of octylchloride present as well, the reaction eixture was ejected from the flask during the heating up to 160° C.

C. When the latter experiment with octylchloride was repeated with an equimolar amount of tetrabutyl phosphonium iodide instead of the tetrabutyl ammonium iodide, the contents of the reaction flask were ejected as they were heated towards 180° C.

D. The reaction was carried out as described in Example 2 but with 59.35g tin powder (0.5g atom), passage of methyl chloride at 100 mls/min for 5 hr, 24.3g (1.0g atom) of magnesium powder and 38.6g (0.1 mole) of tetrabutylphosphonium iodide. The reaction temperature was 160° - 190° C. The passage of methyl chloride gave an exothermic reaction so that no auxiliary heating was needed. About 1g of tetramethyltin (1% yield based on tin added) was collected from the receiver but the reaction residue smelt of dimethyltin dichloride and trimethyl tin chloride. The residue also gave an exothermic reaction with acetone suggesting the presence of a Grignard compound.

SUMMARY OF COMPARATIVE EXAMPLES A - D

Examples A - C show that magnesium, tin and tetra ammonium or phosphonium iodide, in the presence of an alkyl halide or not can give a violent reaction, and Example D shows that in this reaction little organotin is prepared, a major product being a Grignard compound.

I claim:

1. A process for preparing a tetraalkyltin compound which comprises passing an alkyl halide of formula RX where R is an alkyl group of 1 to 4 carbon atoms and X is a halogen selected from the group consisting of chlorine, bromine and iodine atoms, into a heated suspension of metallic material selected from the group consisting of (i) a mixture of zinc and tin, and (ii) an alloy consisting essentially of tin and zinc, the atomic proportion of zinc to tin present in the metallic material being at least 0.5:1, in a liquid at a temperature of 100°-300° C comprising at least one halide selected from the group consisting of organic quaternary ammonium and phosphonium halides and tertiary sulphonium halides, to react said alkyl halide with said metallic material to form the tetraalkyltin which evaporates to produce a vapour effluent comprising the tetraalkyltin compound.

2. A process according to claim 1 wherein the suspension is heated to a temperature of at least the boiling point of the tetraalkyltin compound under the pressure pertaining over the liquid.

3. A process according to claim 1 wherein the suspension is heated to 130° - 180° C.

4. A process according to claim 1 wherein the alkyl halide is a chloride.

5. A process according to claim 2 wherein the alkyl halide is a methyl halide.

6. A process according to claim 5 wherein the alkyl halide is methyl chloride.

7. A process according to claim 1 wherein the atomic proportion of zinc to tin is from 0.5 : 1 to 3 : 1.

8. A process according to claim 7 wherein the proportion is from 1.5 : 1 to 2.5 : 1.

9. A process according to claim 8 wherein the proportion is about 2 : 1.

10. A process according to claim 1 wherein the halide is selected from those of formula $R'_4 N^+ Y^-$ and $R'_4 P^+ Y^-$, wherein each R' is selected from the group consisting of alkyl groups of 1 to 12 carbon atoms and aralkyl hydrocarbyl groups of 7 to 19 carbon atoms and Y is selected from the group consisting of chloride, bromide and iodide ions.

11. A process according to claim 8 wherein the halide is of formula $R'_4 P^+ Y^-$ wherein each R' is an alkyl group of 1 to 6 carbon atoms and Y is a chloride, bromide or iodide ion.

12. A process according to claim 1 wherein there is an iodide present in the liquid during the reaction.

13. A process according to claim 1 wherein in the suspension the only organic liquid is molten quaternary ammonium or phosponium halide.

14. A process according to claim 3 wherein the alkyl halide is methyl chloride.

15. A process according to claim 12 wherein the alkyl halide is methyl chloride and the metallic material is solid tin and solid zinc.

16. A process according to claim 10 wherein the atomic proportion of zinc to tin is 0.5 : 1 to 3 : 1 and the alkyl halide is a methyl halide.

17. A process according to claim 16 wherein the atomic proportion of zinc to tin is 1.5 : 1 to 2.5 : 1 and the alkyl halide is methyl chloride.

18. A process according to claim 17 wherein gaseous methyl chloride is passed into a suspension of solid zinc and solid tin in an atomic proportion of 1.5 : 1 to 2.5 : 1 in a molten salt selected from the group consisting of salts of formula $R_4' N^+ Y^-$ and $R_4' P^+ Y^-$, wherein each R' is an alkyl group of 1 to 6 carbon atoms and $Y^-$ is a halogen selected from the group consisting of chloride, bromide and iodide ions, at 130° - 180° C to give a gaseous effluent comprising tetramethyltin which is separated from the effluent by condensation.

19. The process according to claim 18 wherein the salt is of formula $R'_4 P^+ Y^-$.

20. A process according to claim 1 wherein said alkyl halide is passed continuously or continually into the heated suspension with continuous collection of said vapour effluent comprising tetraalkyltin.

21. A process according to claim 20 wherein the suspension is at a temperature of at least the boiling point of the tetraalkyltin compound under the pressure pertaining over the liquid.

22. A process according to claim 20 wherein the suspension is heated to 130° - 180° C.

23. A process according to claim 20 wherein the alkyl halide is methyl chloride or ethyl chloride.

24. A process according to claim 20 wherein the halide is selected from those of formula $R'_4 N^+ Y^-$ and $R'_4 P^+ Y^-$, wherein each R' is selected from the group consisting of alkyl groups of 1 to 12 carbon atoms and aralkyl hydrocarbyl groups of 7 to 19 carbon atoms and Y is selected from the group consisting of chlorine, bromide and iodide ions.

25. A process according to claim 22 wherein the alkyl halides is methyl chloride.

26. A process according to claim 25 wherein gaseous methyl chloride is passed continuously or continually into a suspension of solid zinc and solid tin in an atomic proportion of 1 : 1 to 3 : 1 in a molten halide selected from the group consisting of salts of formula $R_4' N^+ Y^-$ and $R_4' P^+ Y^-$, wherein each R' is an alkyl of chloride, bromide and iodide ions, at 130° - 180° C and continuously collecting a gaseous effluent comprising tetramethyltin, which is separated from the effluent by condensation.

27. A process according to claim 13 wherein the alkyl halide is methyl chloride and the metallic material is solid tin and solid zinc.

28. A process according to claim 1 wherein the ratio of said halide selected from the group consisting of organic quaternary ammonium and phosphonium halides and tertiary sulphonium halides to tin, is at least 0.1:1.

* * * * *